(12) United States Patent
Kaneko et al.

(10) Patent No.: US 6,683,083 B1
(45) Date of Patent: Jan. 27, 2004

(54) ANTICANCER AGENTS

(75) Inventors: Noboru Kaneko, 23-12-403, Kasuga 2-chome, Bunkyo-ku, Tokyo 112-003 (JP); Kazuto Nishio, Chiba (JP)

(73) Assignee: Noboru Kaneko (JP)

( * ) Notice: Subject to any disclaimer, the term of this patent is extended or adjusted under 35 U.S.C. 154(b) by 0 days.

(21) Appl. No.: 10/089,718

(22) PCT Filed: Sep. 29, 2000

(86) PCT No.: PCT/JP00/06786

§ 371 (c)(1), (2), (4) Date: Aug. 2, 2002

(87) PCT Pub. No.: WO01/22968

PCT Pub. Date: Apr. 5, 2001

(30) Foreign Application Priority Data

Sep. 30, 1999 (JP) .............................. 11-280874

(51) Int. Cl.[7] .................. A61K 31/496; A61P 35/00; C07D 211/52; C07D 217/04
(52) U.S. Cl. .................. 514/253.01; 514/253.05; 544/363; 544/359
(58) Field of Search ................ 544/363, 359; 514/253.05, 253.01

(56) References Cited

U.S. PATENT DOCUMENTS 5,304,558 A * 4/1994 Kaneko et al. ........ 514/253.05

FOREIGN PATENT DOCUMENTS

WO  9200962  1/1992

* cited by examiner

Primary Examiner—Mukund J. Shah
Assistant Examiner—Hong Liu

(74) Attorney, Agent, or Firm—Ostrolenk, Faber, Gerb & Soffen, LLP

(57) ABSTRACT

Disclosed herein is a method for suppressing the growth of cancer cells in a mammal in need of such treatment comprising administering to said mammal a cancer cell suppressing amount of a diphenylmethylpiperazine represented by the following general formula [1]:

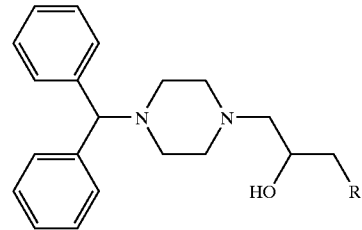

wherein R represents:

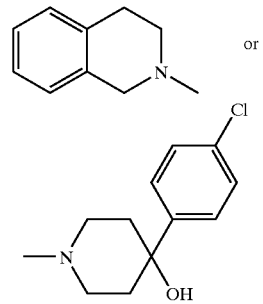

or a pharmaceutically acceptable salt thereof.

Compared with conventional anticancer agents, these agents are less toxic and exert an excellent carcinostatic effect on various solid cancers. Moreover, these anticancer agents inhibit the proliferation of fibroblasts, which makes them efficacious against pulmonary fibrosis and proliferative keloid lesions.

6 Claims, 1 Drawing Sheet

ANTICANCER AGENTS

TECHNICAL FIELD

The present invention relates to an anticancer agent, i.e. an anti-malignant tumor agent, for suppressing cancer growth, and more particularly, to an anticancer agent, i.e. an anti-malignant tumor agent, containing diphenylmethylpiperazine derivatives and for suppressing the growth of cancer cells of mammals including human. The present invention also relates to a fibrosis inhibitor for treating proliferative lesions of pulmonary fibrosis (fibroid lung) disease due to fibroblastic proliferation and pulmonary fibrosis disease due to fibroblastic proliferation as side effects of anticancer agents, and more particularly, to a fibrosis inhibitor containing diphenylmethylpiperazine derivatives and for treating proliferative lesions of mammals including human.

BACKGROUND ART

Anticancer agents or anti-malignant tumor agents include (1) a nitrogen mustard group, such as melphalan, mechlorethamine and cyclophosphamide, (2) a nitrosourea group, such as BCNU, CCNU, methyl-CCNU and ACNU, (3) an azirine group and an epoxide group, such as thiotepa, mitomycin AZQ, carboquone, dianhydrogalactitol and dibromodulcitol, (4) alkylating agents, such as procarbazine, dacarbazine, and hexamethylenmelamin, (5) antimetabolites including methotrexate (MTX), 6-mercaptopurine (6-MP), 6-thioguanine (6-TG), and 5-fluoropyrimidine such as 5-fluorouracil (5-FU), tegafur, UFT, 5'-DFUR and HCFU, and analogue compounds thereof, (6) anticancer agents derived from plants including vinca alkaloid compounds such as vincristine, vinblastine and vindesine, etoposide compounds such as etoposide and teniposide, a taxane group such as paclitaxel and docetaxel, and camptothecin compounds such as irinotecan, (7) anticancer antibiotics such as adriamycin, serbidine, actinomycine D, cosmegen, prenoxanthan, mutamycin, metamycin, and novantron, (8) hormone agents such as adeno-corticoid, estrogen, progesterone, antiestrogen, aromatase inhibitor, androgen, antiandrogen and LH-RH analogues, (9) enzymes such as L-asparaginase, (10) platinum complex compounds such as cisplatin, carboplatin and nedaplatin (254-S), (11) nonspecific immunostimulants, (12) interferon, and (13) a TNF group.

Along with the establishment of medical treatments by the use of these anticancer agents, a patient of acute lymphatic leukemia, Hodgkin's disease or the like has had considerably high possibility of returning to social life. However, a patient involved with solid cancers, such as gastric cancer, lung cancer and colon cancer, largely relies upon surgical and radiation treatments. Cisplatin has been used in the treatments of these solid cancers because of its broad antitumor spectrum. However, cisplatin has a problem of confirmed toxicities, such as nephrotoxicity, gastrointestinal toxicity, auditory toxicity and peripheral nerve toxicity, and its low cure rate.

Further, it is known that some anticancer agents superinduce pulmonary fibrosis as side effects, which has serious impact on life prognosis.

It is an object of the present invention to solve these problems of the anticancer agents.

It is an object of the present invention to provide compounds, salts thereof and derivatives thereof, which have a property of exhibiting a significant anticancer activity (or anti-malignant tumor activity) against various cancers or suppressing proliferation of pulmonary fibroblast, or combinedly have both properties of exhibiting a significant anticancer activity (or anti-malignant tumor activity) against various cancers and suppressing proliferation of pulmonary fibroblast, as well as a desirable low toxicity.

DISCLOSURE OF INVENTION

The inventors have discovered that compounds represented by the following general formula [1];

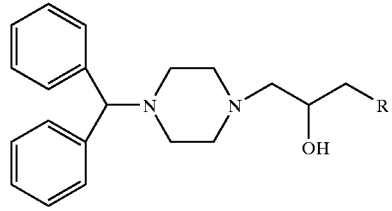

wherein R represents;

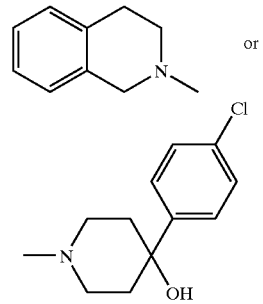

salts thereof, derivatives thereof or prodrugs thereof have a less toxicity than that of cisplatin, and have a greater carcinostatic effect on various cancers and fibroblastic proliferation suppressing effect than those of cisplatin, and have then completed the present invention.

That is, the present invention is an anticancer agent containing a compound represented by the following general formula [1];

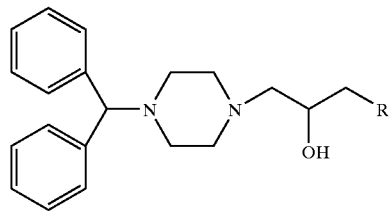

wherein R represents;

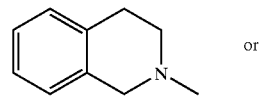

-continued

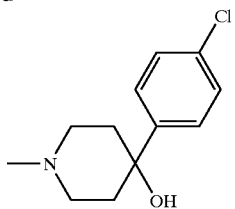

a salt thereof, a derivative thereof or a prodrug thereof.

BEST MODE FOR CARRYING OUT THE INVENTION

Figure 1:
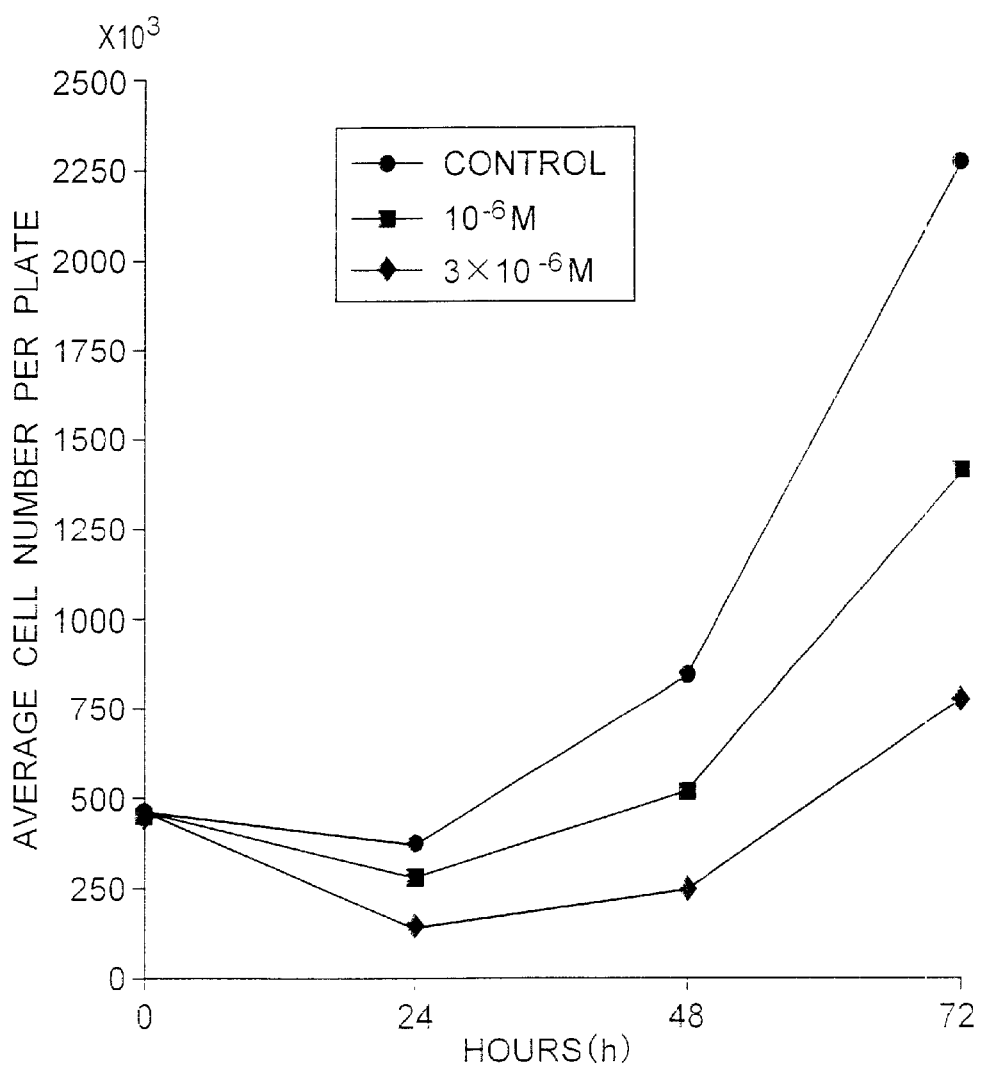
FIG. 1 is a graph showing a cell-proliferation suppressing action against fibroblast of the compound represented by the above general formula [1] and the like shown in Example 2.

A compound represented by the following general formula [1];

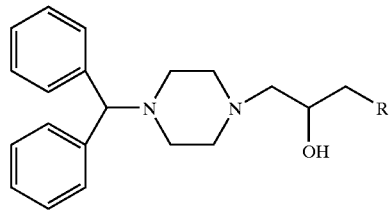

wherein R represents;

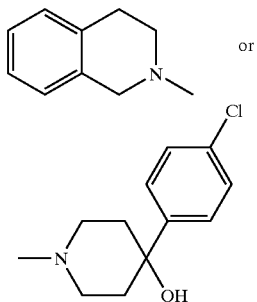

(hereinafter referred to as "the compound represented by the above general formula [1]"), a salt thereof, a derivative thereof or a prodrug thereof (hereinafter, all together, referred to as "the compound represented by the above general formula [1] and the like) and a method for manufacturing the same of the present invention are disclosed in: International Patent Laid-Open Publication WO-92/00962 and Japanese Patent Laid-Open Publication No. Hei 4-69377 (hereinafter referred to as "the above publications").

The above publications further disclose that the compound represented by the above general formula [1] and the like have an action of suppressing myocardial hypercontraction and hyperextension to protect cardiac muscle myocardium from necrosis without any cardiac depression action, and have an effect of curing and preventing cardiac infarction as well as an effect of suppressing and preventing myocardial necrosis.

The inventors have discovered that, compared with cisplatin and other anticancer agents, the compound represented by the above general formula [1] and the like have a superior anticancer action against various cancers and exhibit a broader anticancer spectrum against various cancers in vivo and in vitro. The inventors have also discovered that the compound represented by the above general formula [1] and others suppressed proliferation of fibroblasts.

In the present invention, the term "anticancer agent" encompasses any cures or therapeutic agents of cancers, and/or any fibrosis inhibitors or suppressors.

In the present invention, the "salt" of the compound represented by the above general formula [1] means any pharmaceutically acceptable salts, and includes, but is not limited to, inorganic acid addition salts such as hydrochloride, hydrobromide, sulfate, phosphate or nitrate; organic acid addition salts such as acetate, propionate, succinate, glycolate, lactate, malate, oxalate, tartrate, citrate, maleate, fumarate, methanesulfonate, benzenesulfonate, p-toluenesulfonate or ascorbate; or amino acid addition salts, such as aspartate or glutamate, as well as hydrated substances and hydrates.

In the present invention, the "prodrug" of the compound represented by the above general formula [1] is any derivative of the compound represented by the above general formula [1], in which the derivative has a chemically or metabolically degradable group, and exhibits an activity as an anticancer agent by hydrolysis or solvolysis or by degradation under physiological conditions.

The compound represented by the above general formula [1] and the like according to the present invention has an excellent carcinostatic effect. More specifically, the anticancer agent according to the present invention contains at least one of the compounds represented by the above general formula [1] and the like as a principal agent. The anticancer agent of the present invention can be administered together with any other suitable anticancer agent to bring out an enhanced carcinostatic action even against cancers having an acquired resistance. When used as an anticancer agent, the compound represented by the above general formula [1] and the like may be typically administered systemically or locally, or orally or parenterally. The anticancer agent of the present invention may be administered simultaneously with any other suitable anticancer agent, or before or after such other anticancer agent is administered.

While the dosage of the anticancer agent is varied according to age, weight, symptom, therapeutic effect, way of administration, treatment time or the like, the anticancer agent is typically administered in the range of 0.01 mg to 1 g, preferably in the range of 100 to 500 mg, per adult (average weight of 60 kg), orally or parenterally once a day or in several divided doses a day. In the parenteral administration, the anticancer agent may be continuously administered over 12 hours or more.

When a solid composition for oral administration is prepared by using the compound represented by the above general formula [1] and the like of the present invention as a principal agent, the solid composition may be formed in any suitable dosage form, such as tablet, pill, powder or granule. In such a solid composition, one or more principal agents may be mixed with one or more active diluents, dispersants, adsorbents or the like, such as lactose, mannitol, glucose, hydroxypropylcellulose, microcrystalline cellulose, starch, polyvinylpyrolidone, magnesium aluminometasilicate or silicic acid anhydride powder. Further, the composition may be mixed with any suitable additive other than the diluents in the usual manner.

For preparing the tablet or pill by using the compound represented by the above general formula [1] and the like of the present invention as a principal agent, the tablet or pill may be coated with a film made of a gastric-soluble or enteric-soluble substance, such as saccharose, gelatin, hydroxypropylcellulose or hydroxymethylcellulose phthalate, or may be coated with two or more layers, according to need. Further, the tablet or pill may be capsuled by any suitable substance such as gelatin or ethylcellulose.

When a liquid composition for oral administration is prepared by using the compound represented by the above general formula [1] and the like of the present invention as a principal agent, the liquid composition may be formed in any suitable pharmaceutically acceptable dosage form, such as emulsion, solution, suspension, syrup or elixir. In this case, a diluent to be used includes, for example, purified water-ethanol, vegetable oil or emulsifier or the like. In addition to the diluent, such a composition may be mixed with an adjuvant, such as a moistening agent, suspension, edulcorant, flavoring ingredient, aromatic substance or antiseptic.

When a solution for injection for parenteral administration is prepared by using the compound represented by the above general formula [1] and the like of the present invention, a sterile aqueous or non-aqueous solution, solubilizing agent, suspension or emulsifier may be used. The aqueous solution, solubilizing agent or suspension includes, for example, water for injection, distilled water for injection, physiological salt solution, cyclodextrin and derivatives thereof, an organic amine group such as triethanolamine, diethanolamine, monoethanolamine or triethylamine, or an inorganic alkali solution.

For preparing the water-soluble solution by using the compound represented by the above general formula [1] and the like of the present invention, for example, propylene glycol or polyethylene glycol; or vegetable oil such as olive oil; or alcohol such as ethanol may be used. Further, the solubilizing agent includes, for example, a surface-active agent (for forming mixed micelle) such as polyoxyethylene hydrogenated castor oil, or saccharose fatty acid ester; or lecithin or hydrogenated lecithin (for forming liposome). Further, an emulsion formulation may be formed by composed of non-aqueous solvent such as vegetable oil, and lecithin, polyoxyethylene hydrogenated castor oil, polyoxyethylene-polyoxypropyleneglycol or the like.

Other compositions for parenteral administration may be formed in a liniment such as ointment, a suppository, a pessary or the like, which contains one or more principal agents, i.e. the compound represented by the above general formula [1] and the like, and is prescribed according to a known method.

EXAMPLES

Examples of a formulation using the compound represented by the above general formula [1] and the like of the present invention as a principal agent of an anticancer agent will be specifically described below. However, this invention is not limited by the following description.

Example 1

An injection formulation of an anticancer agent in this example uses 1-[1-4-(diphenylmethyl)piperazinyl]-3-[1-{4-(4-chlorophenyl)-4-hydroxy}piperidinyl]-2-propanol (hereinafter referred to as "compound 1") as a principal agent.

Examples of synthesizing compound 1 will be described below. In the following description, the nuclear magnetic resonance spectrum (NMR) is measured by using tetramethylsilane as an internal standard, and is expressed by ppm. The unit "part" means "volume part".

(1) Synthesis of 1-(Diphenylmethyl)-4-(1-(2,3-epoxy)propyl)piperazine

After 1-(diphenylmethyl)piperazine (10.0 g) was dissolved in acetonitrile (50 ml), sodium carbonate (6.5 g) and epibromohydrin (6.8 g) were added thereto, and the mixture was heated under reflux for 2.5 hours. Salts were separated by filtration, and then the resulting filtrate was concentrated under reduced pressure. The resulting residue was purified by silica gel column chromatography (Wako gel C-200, 200 g) and eluted with a mixed solvent of 99 parts of chloroform and 1 part of methanol to obtain 1-(diphenylmethyl)-4-(1-(2,3-epoxy)propyl)piperazine (5.9 g).

Nuclear Magnetic Resonance Spectrum $^1$H-NMR (CDC13, 500 MHz) δ: 2.30–2.80 (12H, m), 3.06–3.10 (1H, s), 4.23 (1H, s), 7.16 (2H, t, J=7.3 Hz), 7.25 (4H, t, J=7.3 Hz), 7.40 (4H, d, J=7.3 Hz).

(2) Synthesis of 1-{1-4-(Diphenylmethyl) piperazinyl}-3-[1-{4-(4-chlorophenyl)-4-hydroxy}piperidinyl]-2-propanol 1-(diphenylmethyl)-4-(1-(2,3-epoxy)propyl)piperazine (3.0 g) and 4-(4-chlorophenyl)-4-hydroxypiperidine (2 g) were dissolved in o-dichlorobenzene (20 ml), and heated under reflux for 2.5 hours. After standing to cool, the mixture was purified by silica gel column chromatography (Wako gel C-200, 100 g) to obtain 4.6 g of 1-{1-4-(diphenylmethyl)piperazinyl}-3-(1-{4(4-chlorophenyl)-4-hydroxy}-piperidinyl]-2-propanol (compound 1).

Infrared Absorption Spectrum: IR νmax (cm−1) KBr: 3300, 2950, 2650, 1620, 1450, 1100, 910, 830, 750, 710 (as hydrochloride)

Nuclear Magnetic Resonance Spectrum $^1$H-NMR (CDC13, 500 MHz) δ: 1.50~1.90 (4H, m), 2.01~2.21 (2H, m), 2.30~2.55 (10H, m), 2.80~2.90 (2H, m), 3.87~3.93 (1H, m), 4.22 (1H, s), 7.16 (2H, t, J=7.3 Hz), 7.26 (4H, t, J=7.3 Hz), 7.30 (2H, d, J=8.5 Hz), 7.40 (4H, d, J=7.3 Hz), 7.42 (2H, d, J=8.5 Hz).

FD Mass Spectrum

FD-MS (m/z): 519, 521 (M+).

| (1) Injection Formulation of Compound 1 | |
| --- | --- |
| compound 1 | 2–40 mg |
| D-sorbitol | 1000 mg |
| citric acid | 10 mg |
| sodium hydroxide | optimum dose |
| water for injection | to obtain 20.0 ml of solution by adding water for injection |

D-sorbitol and citric acid were dissolved in a sufficient amount of water for injection. Compound 1 was dissolved in the obtained solution, and the resulting solution was adjusted to pH 3.2–3.3 by adding sodium hydroxide. Then, the remaining water for injection was added thereto under agitation. This solution was filtered and then hermetically filled into an ampoule of 20 ml. The contents of the ampoule were sterilized in an autoclave.

(2) Verification of In Vitro Antitumor Effects on Various Human Cancer Cell Lines According to the MTT Assay Method.

Each single cell of a human non-small-cell lung cancer cell line PC-14, a human non-small-cell lung cancer cell line SBC-3, a human non-small-cell mammary cancer cell line MCF-7, a human non-small-cell ovarian cancer cell line SKOV3, a human leukemia cell line HL60 and a human colon cancer cell line WiDR was obtained by trypsinization or by using a cell scraper in RPMI 1640 medium to prepare a suspension containing 100 cells per 15 $\mu$l. The compound 1 as an anticancer agent was dissolved in dimethylsulfoxide and then the solution was added to the suspension to make the concentration of the compound fall within a range between 0.5 and 1 $\mu$M, and the resulting suspension was poured into a 96-perforated plate at 150 $\mu$l/well. This plate was maintained at a temperature of 37° C. under 5% of carbon dioxide and saturated vapor for 96 hours to incubate the suspension. After incubation, the incubated suspension was combined with 20 $\mu$l of MTT (3-(4,5-dimethylthiazol-2-yl)-2,5-diphenyltetrazoliumbromide) reagent dissolved in D-PBS (−) at a concentration of 5 mg/ml, and was further incubated at 37° C. for 4 hours. After the completion of incubation, the entire plate was centrifuged to discharge supernatant. Then, 200 $\mu$l of dimethyl sulfoxide was added to dissolve purple formazan which is created from yellow MTT by the action of dehydrogenase lying in mitochondria in the cancer cell, and the amount of the created formazan was determined by reading the absorbance at a wave length ranging from 562 to 630 nm with a multi-plate reader. Given that the average growth rate of a negative control is 0% and the average growth rate of a positive control is 100%, a tumor-volume growth curve was plotted, and the concentration of compound 1 required for 50% of human cancer-cell proliferation suppression was calculated. This is shown in Table 1.

TABLE 1

| cell line | amount of compound 1 required to achieve $IC_{50}$ ($\mu$M) |
|---|---|
| PC-14 (human non-small-cell lung cancer cell line) | 1.02 ± 0.20 |
| SBC-3(human small-cell lung cancer cell line) | 0.46 ± 0.03 |
| MCF-7 (human mammary cancer cell line) | 0.60 ± 0.08 |
| SKOV3 (human ovarian cancer cell line) | 0.85 ± 0.02 |
| HL60 (human leukemia cell line) | 1.18 ± 0.05 |
| WiDR (human colon cancer cell line) | 0.41 ± 0.03 |

The values in Table 1 indicate each value of the concentration required for 50% of human cancer-cell proliferation suppression from the MTT assay in triple culture tests of independent cancer cells using compound 1 by average±error range ($\mu$M).

As shown in Table 1, the compound 1 shows the 50% proliferation suppression effect ($IC_{50}$) against various cancers at a concentration ranging from 0.5 to 1.1 $\mu$M. This $IC_{50}$ value of compound 1 is significantly lower than the $IC_{50}$ value ranging from 2 to 3 $\mu$M in the MTT assay method of cisplatin which has been considered as the most effective agent against solid cancers. According to the $IC_{50}$ of compound 1, it is proved that compound 1 has an enhanced carcinostatic effect and effectiveness as an anticancer agent. In addition, compound 1 exhibits substantially equal anti-tumor effects on solid cancer cells such as lung cancer, mammary cancer, colon cancer, ovarian cancer, as well as leukemia cells. This means that compound 1 has a broad antitumor spectrum.

Example 2

Nine plates were prepared for each of control and compound 1 groups each having a concentration of $1 \times 10^{-6}$ M and a compound 1 group having a concentration of $3 \times 10^{-6}$ M (total of 27 plates). The number $4.4 \times 10^{5}$ of fibroblasts NIH3T3 were added to each of the 27 plates, and D-MEM culture solution added with 10% FBS (fetal bovine serum) was added thereto. Each of the controls was incubated with added water corresponding to the added amount of compound 1. The number of cells in 3 plates of each of the groups was measured every 24 hours, and the measured numbers were averaged to provide an average cell number per plate. The results are shown in FIG. 1. As shown in the results, the compound 1 has an effective anticancer action and effectiveness to proliferative lesions such as interstitial pneumonia and keloid due to proliferation of fibroblasts.

Example 3

A physiological saline suspension was made by adding $2 \times 10^{7}$ cells of human non-small-cell lung cancer cell line PC-14, and was then implanted subcutaneously to the back of female nude mice BALB/c nu/nu (6 weeks). Then, progress of take was observed. The seventh day after the implantation, the tumor state was checked to select testable mice. The selected mice were randomized to avoid deviation, and divided into a control group, a first subject group and a second subject group each composed of 6 mice. Each tumor volume of the implanted tumors was determined by measuring the minor axis and the major axis of each tumor and then calculating the product of square of the minor axis of the tumor and the major axis of the tumor, i.e. using the formula: (the minor axis of the tumor)$^2$×(the major axis of the tumor). From the seventh day after the tumor implantation, the administration of the compound 1 was started.

1.2 mg of the compound 1 was dissolved in 0.05 ml of dimethyl sulfoxide, and 0.95 ml of solution consisting of 5% sorbitol-0.2% citric acid 1 hydrate (pH 3.3) was added thereto to form a uniform solution as a solution for injection.

For six subjects of the group number 1, the compound 1 was administered by injecting from each tail of the nude mice on each of the 7th, 8th, 10th and 11th days after the implantation, at 3 mg of the compound 1 per kg of weight once a day. For six subjects of the group number 2, the compound 1 was administered by injecting from each tail of the nude mice on each of the 7th, 8th, 10th and 11th days after the implantation, at 5 mg of the compound 1 per kg of weight once a day. The subjects of the group number 1 to be the controls were a group having no administration of the compound 1, and neither administration nor treatment of the compound 1 was performed on the controls. For all of the subjects, the state of each entire body of the mice was observed to measure each weight and tumor volume of the mice, once a day from the 1st day to the 8th day after the administration of compound 1, before the compound 1 was administered. In the result of the observation of each entire body state of the mice and the measurement of each weight of the mice, substantially no difference was found between the subjects of the group numbers 1 to 3. However, in the result of each tumor volume of the mice, a specific difference was found between the subjects of the group numbers 1 to 3. The measurement of the tumor volumes is shown in the following Table 2, and the average of the tumor volumes in each of the groups is shown in Table 3. In Tables 2 and 3, each size of the tumor volumes after the 2nd day is represented on condition that the size of the tumor volume on the 1st day is 100.

TABLE 2

| group No. | subject No | 1 day | 2 day | 3 day | 4 day | 5 day | 6 day | 7 day | 8 day |
|---|---|---|---|---|---|---|---|---|---|
| 1 | 1 | 100.00 | 111.45 | 148.16 | 179.50 | 233.01 | 208.06 | 230.37 | 290.31 |
| 1 | 2 | 100.00 | 145.96 | 116.07 | 117.73 | 107.15 | 61.17 | 108.09 | 131.77 |
| 1 | 3 | 100.00 | 103.15 | 71.62 | 72.94 | 74.51 | 55.21 | 72.46 | 60.61 |
| 1 | 4 | 100.00 | 169.32 | 143.35 | 149.41 | 205.18 | 214.09 | 221.72 | 265.04 |
| 1 | 5 | 100.00 | 91.66 | 140.09 | 114.08 | 111.79 | 188.97 | 165.66 | 182.55 |
| 1 | 6 | 100.00 | 131.69 | 147.32 | 85.63 | 132.46 | 87.52 | 113.77 | 127.27 |
| 2 | 1 | 100.00 | 45.35 | 20.22 | 46.17 | 31.44 | 30.93 | 52.68 | 56.49 |
| 2 | 2 | 100.00 | 120.51 | 98.14 | 80.18 | 66.58 | 122.90 | 99.04 | 127.45 |
| 2 | 3 | 100.00 | 139.67 | 85.27 | 105.01 | 67.76 | 55.16 | 75.58 | 130.56 |
| 2 | 4 | 100.00 | 73.21 | 52.91 | 42.19 | 22.55 | 0.00 | 0.00 | 0.00 |
| 2 | 5 | 100.00 | 73.29 | 62.47 | 31.02 | 18.55 | 10.11 | 12.98 | 4.97 |
| 2 | 6 | 100.00 | 66.68 | 83.06 | 85.73 | 51.09 | 51.30 | 47.68 | 30.49 |
| 3 | 1 | 100.00 | 55.40 | 58.27 | 79.34 | 47.44 | 33.96 | 34.07 | 47.99 |
| 3 | 2 | 100.00 | 63.47 | 43.51 | 40.73 | 40.65 | 32.21 | 36.27 | 15.80 |
| 3 | 3 | 100.00 | 93.53 | 72.22 | 83.65 | 62.95 | 54.93 | 86.76 | 102.87 |
| 3 | 4 | 100.00 | 68.25 | 113.73 | 123.79 | 103.32 | 135.18 | 129.59 | 140.33 |
| 3 | 5 | 100.00 | 90.42 | 70.23 | 36.86 | 28.95 | 14.65 | 17.36 | 7.22 |
| 3 | 6 | 100.00 | 80.68 | 92.68 | 84.55 | 79.20 | 51.96 | 85.12 | 61.54 |

TABLE 3

| group No. | average (6 mice) | 1 day | 2 day | 3 day | 4 day | 5 day | 6 day | 7 day | 8 day |
|---|---|---|---|---|---|---|---|---|---|
| 1 | 1 | 100.00 | 121.23 | 124.35 | 121.20 | 147.83 | 143.83 | 159.88 | 165.10 |
| 2 | 2 | 100.00 | 89.79 | 67.01 | 68.38 | 46.68 | 47.73 | 42.99 | 58.33 |
| 3 | 3 | 100.00 | 78.63 | 75.11 | 74.99 | 60.45 | 53.82 | 64.86 | 62.63 |

1-{1-4-(Diphenylmethyl)piperazinyl}-3-[1-{4-(4-chlorophenyl)-4-hydroxy}piperidinyl]-2-propanol In view of the results of the examples 1 to 3, it is proved that the compound 1 has a high carcinostatic effect.

While the compound 1 of 1-{1-4-(diphenylmethyl) piperazinyl}-3-[1-{4-(4-chlorophenyl)-4-hydroxy}piperidinyl]-2-propanol was used as a principal agent in the above examples 1 to 3, 1-{2-(1,2,3,4-tetrahydro) isoquinolinil}-3-{1-(4-diphenylmethyl)piperidinyl}-2-propanol was used as a principal agent to obtain the same result.

A example of synthesizing 1-{2-(1,2,3,4-tetrahydro) isoquinolinil}-3-{1-(4-diphenylmethyl)piperidinyl}-2-propanol will be described bellow. In the following description, a nuclear magnetic resonance spectrum (NMR) is measured by using tetrametylsilane as an internal standard, and expressed by ppm. The unit "part" means "volume part".

Example 4

(1) Synthesis of 2-{1-(2,3-Epoxy)propyl}-1,2,3,4-tetrahydroisoquinoline 1,2,3,4-tetrahydroisoquinoline (25.0 g) was dissolved in acetonitrile (100 ml), and sodium carbonate (40.0 g) and epibromohydrin (31.0 g) were added thereto. Then, the mixture was heated under reflux for 4 hours. After separating salts in the mixture by filtration, the filtrate was concentrated under reduced pressure. The resulting residue was purified by silica gel column chromatography (Wako gel C-200, 500 g), and then was eluted with a mixed solvent of 99 parts of chloroform and 1 part of methanol to obtain 2-{1-(2,3-epoxy) propyl}-1,2,3,4-tetrahydroisoquinoline (15.6 g).

Nuclear Magnetic Resonance Spectrum $^1$H-NMR (CDC13, 100 MHz) δ: 2.36~2.60 (2H, m), 2.73~3.03 (6H, m), 3.09~3.29 (1H, m), 3.65 (1H, d, J=14.9 Hz), 3.83 (1H, d,).

(2) Synthesis of 1-{2-(1,2,3,4-Tetrahydro) isoquinolinil}-3-{1-(4-diphenylmethyl)piperazinyl}-2-propanol 2-{1-(2,3-epoxy)propyl}-1,2,3,4-tetrahydroisoquinoline (3.0 g) and 1-(diphenylmethyl)piperazine (4.4 g) were dissolved in o-dichlorobenzene (20 ml), and heated under reflux for 2.5 hours. After standing to cool, the mixture was purified by silica gel column chromatography (Wako gel C-200, 150 g) to obtain 1-{2-(1,2,3,4-tetrahydro) isoquinolinil}-3-{1-(4-diphenylmethyl)piperazinyl}-2-propanol (6.0 g).

Infrared Absorption Spectrum: IR νmax (cm−1) KBr: 3400, 3000, 2550, 1620, 1450, 1080, 920, 760, 710 (as hydrochloride).

Nuclear Magnetic Resonance Spectrum $^1$H-NMR (CDC13, 100 MHz) δ: 2.30~2.60 (1.2H, m), 2.75~2.95 (4H, m), 3.62~3.80 (2H, m), 3.92~4.03 (1H, m), 4.21 (1H, s), 7.00~7.51 (14H, m).

FD Mass Spectrum

FD-MS (m/z): 441 (M+).

INDUSTRIAL APPLICABILITY

The compound represented by the above general formula [1] and the like according to the present invention have a less toxicity than that of the conventional anticancer agents such as cisplatin, and exhibits a greater carcinostatic action against various cancers and a broader carcinostatic spectrum than that of the conventional anticancer agents. Thus, compared with the conventional anticancer agents, the present invention will make a greater contribution to treatments of cancers (solid cancers) and other malignant tumors. Further, the present invention has an action of suppressing proliferation of fibroblasts such as pulmonary fibrosis, and has an excellent fibrosis suppressing action superior to the conventional curatives of pulmonary fibrosis, keloid or the like. Thus, the present invention will make a greater contribution to treatments of pulmonary fibrosis or keloid.

What is claimed is:

1. A method for suppressing the growth of cancer cells in a mammal in need of such treatment comprising administering to said mammal a cancer cell suppressing amount of a diphenylmethylpiperazine represented by the following general formula [1]:

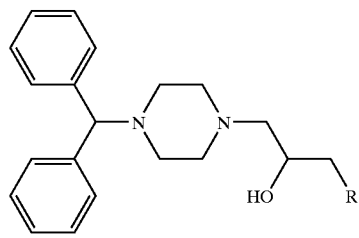

[1]

wherein R represents:

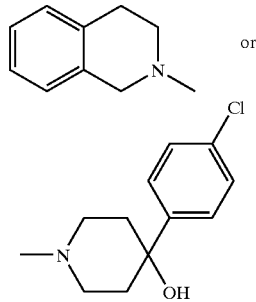

or or a pharmaceutically acceptable salt thereof.

2. The method of claim 1, wherein the diphenylmethylpiperazine is 1-{1-4-(diphenylmethyl)piperazinyl}-3-[1-{4-(4-chlorophenyl)-4-hydroxy}piperidinyl]-2-propanol.

3. The method of claim 1, wherein the diphenylmethylpiperazine is 1-{2-(1,2,3,4-tetrahydro)isoquinolinyl}-3-{1-(4-diphenylmethyl)piperazinyl}-2-propanol.

4. A method for treating proliferative lesions of pulmonary fibrosis disease in a mammal in need of such treatment comprising administering to said mammal a fibrosis inhibiting amount of a diphenylmethylpiperazine represented by the following general formula [1]:

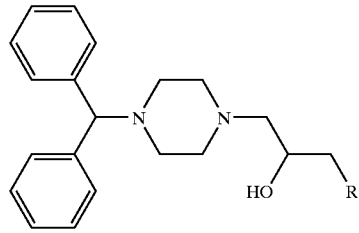

[1]

wherein R represents:

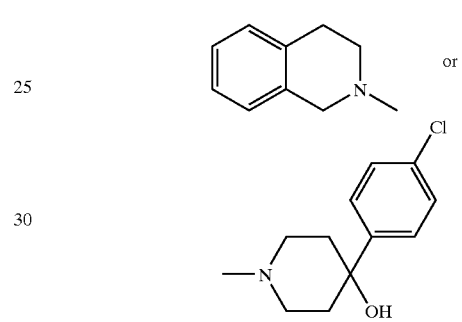

or or a pharmaceutically acceptable salt thereof.

5. The method of claim 4, wherein the diphenylmethylpiperazine is 1-{1-4-(diphenylmethyl)piperazinyl}-3-[1-{4-(4-chlorophenyl)-4-hydroxy}piperidinyl]-2-propanol.

6. The method of claim 4, wherein the diphenylmethylpiperazine is 1-{2-(1,2,3,4-tetrahydro)isoquinolinyl}-3-{1-(4-diphenylmethyl)piperazinyl}-2-propanol.

* * * * *

UNITED STATES PATENT AND TRADEMARK OFFICE
CERTIFICATE OF CORRECTION

PATENT NO. : 6,683,083 B1 Page 1 of 1
APPLICATION NO. : 10/089718
DATED : January 27, 2004
INVENTOR(S) : Noboru Kaneko et al.

It is certified that error appears in the above-identified patent and that said Letters Patent is hereby corrected as shown below:

Column 8, line 40:

Change "group number 1" to --group number 3--.

Column 9, line 39:

Change "examples 1 to 3" to --examples 2 and 3--.

Signed and Sealed this

Eighth Day of May, 2007

JON W. DUDAS
*Director of the United States Patent and Trademark Office*